Figure 1:
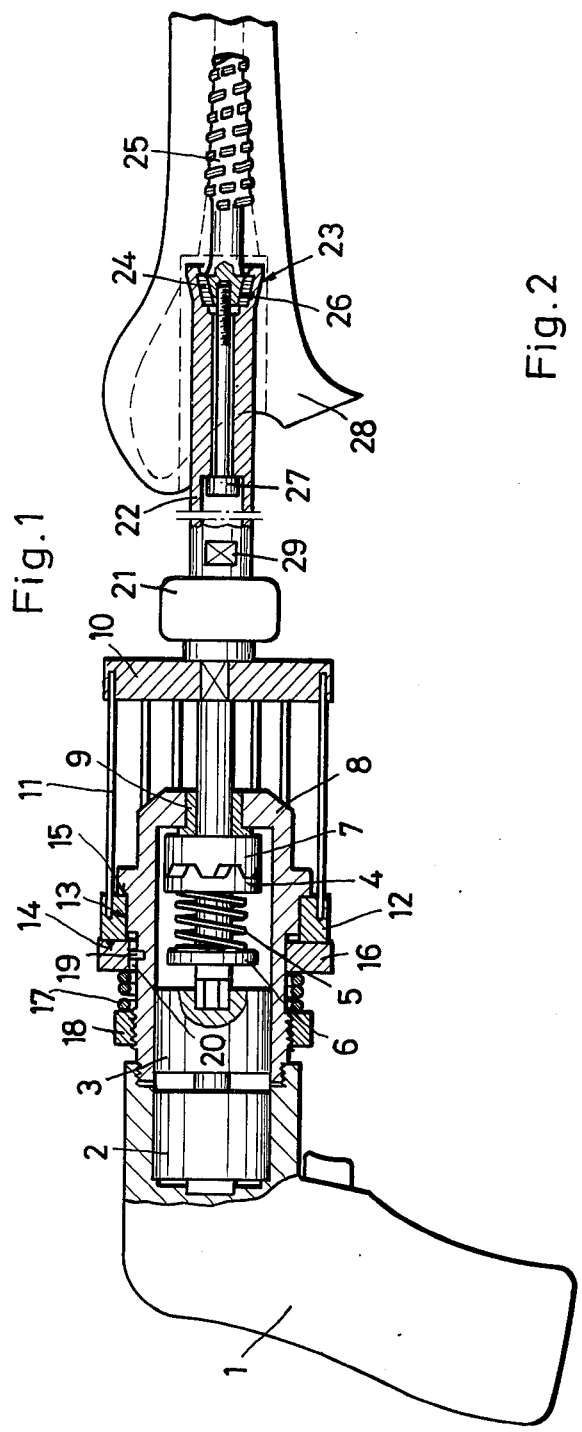

United States Patent [19]

Berner et al.

[11] 4,124,026
[45] Nov. 7, 1978

[54] PROCEDURE AND APPARATUS FOR SCREWING IMPLANTS INTO BONES

[75] Inventors: Karl Berner, Altdorf; Jürgen K. D. Koltermann, Bopfingen; Helmut K. Grell, Aalen, all of Fed. Rep. of Germany

[73] Assignee: Deutsche Gardner-Denver GmbH, Westhausen, Fed. Rep. of Germany

[21] Appl. No.: 795,682

[22] Filed: May 11, 1977

[30] Foreign Application Priority Data

May 14, 1976 [DE] Fed. Rep. of Germany ....... 2621383

[51] Int. Cl.$^2$ .................. A61B 17/00; A61B 17/18
[52] U.S. Cl. .................. 128/303 R; 128/92 BC; 128/92 BB; 128/92 E; 3/1.9; 173/163
[58] Field of Search ............ 128/92 B, 92 BC, 92 BB, 128/92 R, 92 E, 92 EC, 305, 305.1, 303 R; 3/1.9–1.913; 173/163

[56] References Cited

U.S. PATENT DOCUMENTS

| 2,267,925 | 12/1941 | Johnston | 128/92 BB |
| 2,299,268 | 10/1942 | Fisher | 128/303 R |
| 3,322,212 | 5/1967 | Pauley | 173/163 |
| 3,867,932 | 2/1975 | Huene | 128/92 E |

FOREIGN PATENT DOCUMENTS 1,161,507 3/1958 France .................................. 128/92 B

OTHER PUBLICATIONS

"A Motor-Driven Screw Holder and Screw Driver" by George R. Dawson, The Journal of Bone & Joint Surgery, vol. 29, No. 2, Apr. 1947, pp. 527 and 530.

*Primary Examiner*—Ronald L. Frinks
*Attorney, Agent, or Firm*—Michael E. Martin

[57] ABSTRACT

An artificial hinge pin having a self-cutting threaded portion is inserted into a prepared bone with reduced reaction moment by a hand-held power tool which imposes a rotary oscillating movement on the pin during the insertion process. The tool has an output shaft driven by an overriding ratchet type coupling providing repeated impacts to the output shaft. A plurality of elastic rods connected to the output shaft are arranged coaxially around the shaft and are anchored to a rotary brake disk. Braking force on the disk is controlled by an adjustable compression spring. The eigenfrequency of the elastic system comprising the rods and output shaft may be adjusted to the impact frequency of the ratchet coupling.

13 Claims, 2 Drawing Figures

U.S. Patent

Nov. 7, 1978

4,124,026

PROCEDURE AND APPARATUS FOR SCREWING IMPLANTS INTO BONES

The invention concerns a procedure for inserting a medical fastening element into bone. In methods used until now, for example the method for inserting an artificial hinge into the thigh bone, the pin is simply screwed into the bone or is attached by cutting a thread in the bone. Since the mechanical force required for this method is relatively great, particularly the torque necessary for tapping a threaded pin, the patient will object to the extreme pressure during this known procedure which makes the operation extremely difficult. In addition, since this procedure takes a great deal of time, stress on the patent is increased.

A procedure of the type mentioned above, which eliminates these mechanical and operational disadvantages, shall be provided by the invention, wherein the act of tapping the thread in the bone and the act of inserting the fastening element into this thread are combined mechanically to take place at the same time so that the patient is exposed to considerably less total pressure and stress, and the procedure time can be shortened.

According to the invention this problem is solved by screwing the fastening element, such as a threaded pin, into the bone by means of a rotary oscillating movement and a super-imposed thrust motion.

In a preferred embodiment of the procedure according to the invention, for example with the thigh bone, a conical threaded pin is inserted into a corresponding conical recess, which has been previously prepared, in the bone. This pin is moved back and forth with a rotary oscillating movement in such a way that in one direction of rotary movement the pin cuts into the bone, and in the opposite direction of rotary movement the pin is disengaged for the succeeding cutting movement. During the cutting movement, the pin is simultaneously subjected to a thrust acting in the direction of penetration.

Further characteristics of the procedure are given in the following description of an application as well as in the claims.

The invention concerns, in addition, an apparatus for carrying out the procedure according to the invention, wherein an elastic absorption system is provided for generating the oscillating motion.

The apparatus according to the invention has in addition a so-called self-cutting pin which is provided with a cutting surface for performing the self-cutting action. This self-cutting pin is set into rotary oscillation by the apparatus with a superimposed thrusting motion. The cutting surface of the pin causes the thread to be cut into the bone. The degree of rotation, rotary oscillation frequency, and amplitude are tuned preferably to the composition of the bone which is the internal thread carrier so that only a small and tolerable reaction moment acts on this bone.

Further details of the apparatus according to the invention are given in the description of a preferred embodiment taken together with the drawings and the claims.

The advantage of the procedure according to the present invention as well as of the apparatus for carrying out this procedure lies in the fact that only a fraction of the torque, which was previously necessary with the usual tapping and insertion procedure, must be used for inserting a fastener, as for example a threaded pin, into human or animal bones.

Figure 2:
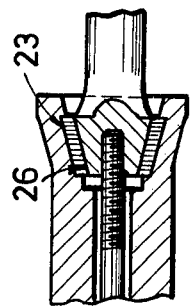

FIG. 1 is a longitudinal section of the apparatus for carrying out the procedure of the present invention; and FIG. 2 shows an enlarged partial section according to FIG. 1.

The oscillating apparatus according to FIG. 1 consists of a familiar power-driven hand-operated tool 1 with electric or pneumatic drive motor 2, gear unit 3, as well as upper ratchet coupling 4, 5, 6, 7 which moreover can be constructed in known ways. The upper ratchet coupling 4–7 is disposed in housing 8. Surrounding the coupling 4–7 there is provided an elastic absorption system which comprises a plurality of elastic rods 11, the driven coupling part 7, and a driven plate 10 fastened to it. The driven plate 10 at the same time forms the outer support for the plurality of elastic rods 11 which are arranged along the longitudinal axis of the motor and the driven plate 10 and are uniformly spaced in a bolt circle around the driven plate.

The tool 1 further comprises a sliding sleeve 21 with a bayonet lock, not shown in detail, a shaft 22, and a fastening screw 27, the thread of which is screwed into the head of a threaded pin 25 to be implanted.

As previously explained, the elastic rods 11 are arranged horizontally in the axial direction in a bolt circle and are mounted on the power takeoff side in the driven plate 10 which forms an elastic rod outer support. On the motor side the rods 11 are fastened in a brake ring 12. This brake ring 12 is slidingly mounted on a brake bearing 13 which, in the example, is a peripheral area of the coupling housing 8. Therefore, the brake ring 12 slides on the coupling housing 8. The radial annular surface of the brake ring 12 facing the motor 2 abuts a radial annular surface 14 formed on a brake friction disk 16. The friction disk 16 is prevented from turning by means of a bolt 19 fastened to coupling housing 8 and projecting into a groove 20 in the friction disk. Therefore, the radial surface 14, against which the brake ring 12 lies, forms a brake surface. The brake pressure itself, which is exerted by the friction disk 16 on the brake ring 12 and thereby acts on the brake surfaces 14 and 15, can be regulated by means of an adjusting nut 18 and a spring 17.

The threaded pin 25 to be implanted has on the drive side a cone 26. The threaded pin 25 is fastened, by means of this cone 26 and the fastening screw 27 inserted into it, into shaft 22 of the tool 1 according to the invention. To decrease the end pressure on cone 26, which is enameled, shaft 22 has a recess 23 which is provided with a packing 24 such as hard plastic for protecting the shaft.

The operation of the apparatus is as follows: Upon engaging drive motor 2, by means of gear 3, the upper ratchet coupling 4–7 will put into clockwise rotation the elastic absorption system components 10, 11, and 12 and the remaining rotating parts 21, 22, 27 driving the threaded pin 25. Through the simultaneous thrust exerted on the tool by the hand, the pin 25 to be implanted moves with this clockwise turning into the bone to a slight degree.

Because of the energy loss of the self-cutting threaded pin 25 which occurs during this clockwise turning and simultaneous thrust motion, the clockwise turning or the forward motion of the self-cutting threaded pin is retarded and stopped rather quickly. During this process, the upper ratchet coupling is disengaged so that a second built-up tension of the elastic rods 11 is active through the rotary mass while the energy accumulated in the elastic rods 11 then lets the rotary mass again swing back into a rotary motion opposite to the thrust rotary motion whereby, after zero passage, the threaded pin 25 is again disengaged. By suitably adjusting the eigenfrequency of the elastic system 7, 10, 11, 21, 22, 25, 27 to the impact frequency of coupling 4–7 of the power-driven hand tool 1, threaded pin 25 and rotary mass 7, 10, 21, 22, 25, 27 will be accelerated again after running through the first rotary oscillation. It has been shown that a rotary oscillating frequency of 50 Hz is a favorable frequency for carrying out the procedure according to the invention.

By a suitable compression of spring 17 against the friction disk 16, the brake ring 12 slides between the rubbing surfaces 14, 15 at the end of each oscillation directed in the forward direction, for example a clockwise oscillarion, whereby an exactly defined, superimposed rotary and thrust motion results. The axial thrust of threaded pin 25 will be produced during cutting of the thread in the initial phase by light pressure and then by the thread pitch.

The advantage of this apparatus lies in the fact that only a very slight, precisely adjustable part of the acting torque enters by way of the threaded pin into the human or animal bone so that stress during the operation is slight. It has been shown that in addition to the preferred rotary oscillation frequency of at least 50 Hz, an angular deflection of the rotary oscillation of $\leq \pm 5°$ is especially suitable.

Before cutting the thread, it is advantageous to rough work the bone in the area of the threading to form a thread-core surface. This is done preferably by milling. During this process, however, only excess bone tissue is removed which is not necessary for the later support function in the thread area. This also facilitates the insertion of the threaded pin or a similar holding or fastening element.

The installation of the fastening part, for example threaded pin 25, into thigh bone 28, takes place as follows: After the thread-core surface has been rough worked in the bone, the initial oscillation of threaded pin 25 takes place with the apparatus according to FIG. 1.

Before the onset of oscillation, the threaded pin 25 to be implanted is inserted with its outer cone 26 in the recess 23 of the shaft 22 and by means of fastening screw 27 is frictionally engaged with the recess.

The shaft 22 for its part is locked by means of sliding sleeve 21 of the bayonet lock and thereby is connected immovably with the oscillating apparatus. The tool, which is now completely ready for the oscillating process, is applied with the threaded pin 25 in front into the prepared bone 28 and actuated. At first, a slight manual axial pressure results until the thread course of threaded pin 25 has cut a slight contour into the bone. After that, the axial thrust results from the cutting of the thread in proportion to the thread pitch. The initial process continues until a definite deep seating of the threaded pin 25 in the bone 28 is attained. After the initial process, the shaft 22 is removed from its setting in the bayonet lock by manual operation of sliding sleeve 21 and the oscillating apparatus is removed. The cone-shaped end 26 of threaded pin 25 to be implanted is now the definite basis for further preparing of the irregularly shaped bone 28. The shaft 22, still connected to threaded pin 25, is now used for further machining on bone 28.

After completion of the foregoing process, the shaft 22 is separated from threaded pin 25 by loosening fastening screw 27.

The reaction moment resulting during the loosening of the screw 27 may be absorbed by means of an auxiliary tool, not shown, applied to the appropriately formed contour 29 of shaft 22.

To the cone-shaped end 26 of implanted pin 25 is now attached the complementary part of the implantation.

We claim:

1. A procedure for inserting a fastening element in bone wherein:
   the fastening element (25) is cuttingly connected to a bone (28) by a rotary oscillating movement with super-imposed thrust movement.

2. A procedure according to claim 1 wherein:
   the bone (28) is prepared by rough working in the area to be tapped until a thread-core surface is formed.

3. A procedure according to claim 1 wherein:
   the rotary oscillating movement is carried out with a frequency of at least 50 Hz.

4. A procedure according to claim 1 wherein:
   the rotary oscillating movement is carried out with an angular deflection of at most $\pm 5°$.

5. A procedure according to claim 1 wherein:
   the fastening element is a threaded pin provided with a thread cutting surface.

6. Apparatus for screwing a fastening element into a bone comprising a motor driven hand-held tool having an overriding clutch comprising a ratchet coupling, an elastic absorption system, which is connected, on the power take-off side of said coupling to a shaft holding a threaded pin by a sliding sleeve.

7. Apparatus according to claim 6 wherein:
   the elastic absorption system comprises a disk-shaped oscillating mass arranged coaxially with respect to the power take-off side of a coupling part of said coupling and is attached to the ends of several rods and comprising a spring, the opposite ends of said rods being connected to a brake ring.

8. Apparatus according to claim 7 wherein:
   said brake ring frictionally abuts a housing of the tool with at least one friction surface.

9. Apparatus according to claim 8 wherein:
   said brake ring is disposed with respect to said housing to have a radial friction area and a bearing surface arranged coaxially with respect to the housing longitudinal axis.

10. Apparatus according to claim 9 wherein:
    a spring, and an adjusting nut are provided for adjusting the amount of brake torque.

11. Apparatus according to claim 10 wherein:
    said spring is arranged between a brake friction disk and said adjusting nut and said friction disk is positively locked to said housing by a bolt disposed in a groove in said friction disk.

12. Apparatus according to claim 7 wherein:
    a positively locking sliding sleeve is provided between said oscillating mass and said shaft.

13. Apparatus according to claim 6 wherein:
    said shaft has a cone-shaped recess for receiving a corresponding cone-shaped end of said threaded pin and a hard plastic packing is disposed in said cone-shaped recess between said recess and said end of said threaded pin.

* * * * *